(12) United States Patent
Ottolini et al.

(10) Patent No.: US 7,051,767 B2
(45) Date of Patent: May 30, 2006

(54) END FORMED TUBE

(75) Inventors: Duane Ottolini, Barto, PA (US); Robert E. Kelly, Pottstown, PA (US)

(73) Assignee: Judson A. Smith Company, Boyertown, PA (US)

( * ) Notice: Subject to any disclaimer, the term of this patent is extended or adjusted under 35 U.S.C. 154(b) by 0 days.

(21) Appl. No.: 10/749,195

(22) Filed: Dec. 30, 2003

(65) Prior Publication Data

US 2005/0145287 A1  Jul. 7, 2005

(51) Int. Cl.
*F16L 11/00* (2006.01)

(52) U.S. Cl. .................. 138/109; 138/178; 29/510; 29/511; 72/370.1

(58) Field of Classification Search ........... 138/177, 138/178, 109; 29/510, 511; 72/370.1
See application file for complete search history.

(56) References Cited

U.S. PATENT DOCUMENTS

| | | | |
|---|---|---|---|
| 994,861 A | 6/1911 | Miller | 138/134 X |
| 1,910,074 A | 5/1933 | Wells | 220/788 |
| 2,288,966 A * | 7/1942 | Blanchet | 242/118.31 |
| 2,849,146 A | 8/1958 | Wigert | 220/40 |
| 3,065,875 A | 11/1962 | Negoro | 220/60 |
| 3,109,590 A * | 11/1963 | Graham | 239/33 |
| 3,828,823 A * | 8/1974 | Douglas | 138/109 |
| 3,881,520 A * | 5/1975 | Murphy | 138/109 |
| 3,948,290 A | 4/1976 | Arisland | 138/89 |
| 4,054,228 A | 10/1977 | Balocca et al. | 220/268 |
| 4,202,462 A | 5/1980 | Imber | 220/293 |
| 4,804,733 A * | 2/1989 | Bataille | 428/34.9 |
| 4,893,657 A | 1/1990 | Usui | 138/109 |
| 5,313,934 A | 5/1994 | Wiita et al. | 128/4 |
| 5,649,662 A | 7/1997 | Krichau et al. | 228/128 |
| 5,989,183 A | 11/1999 | Reisdorf et al. | 600/156 |
| 6,318,410 B1 | 11/2001 | Miyajima et al. | 138/109 |
| 6,889,711 B1 * | 5/2005 | Vetoretti et al. | 138/38 |
| 2004/0140010 A1 * | 7/2004 | Hasslberger et al. | 138/123 |

FOREIGN PATENT DOCUMENTS

EP          154104 A2 *  9/1985

* cited by examiner

*Primary Examiner*—Patrick Brinson
(74) *Attorney, Agent, or Firm*—John J. Penny, Jr.; Edwards Angell Palmer & Dodge LLP

(57) ABSTRACT

An end formed tube to which a molded plastic part is attached and sealed. One end of the end formed tube is rolled over to form a lip, which prevents the removal of the molded part. The rolled over lip portion creates a void in which plastic overmold from the plastic part is deposited, thereby creating a positive seal and attachment. The end of the tube in which the lip is formed is configured in a polygonal shape to provide torsional strength to the interface of the molded part and the tube.

8 Claims, 2 Drawing Sheets

END FORMED TUBE

BACKGROUND OF THE INVENTION

1. Field of the Invention

The present invention relates generally to an end formed tube to which a plastic molded part is attached.

2. Background

Molded plastic parts, or clevis mechanisms, are commonly attached to the end of narrow metal tubes for various applications. For example, one application for such a configuration is an end formed tube having a transparent plastic lens attached thereto. There are many other types of overmolding that can be attached to an end formed tube, such as bearing retainers, drive shaft mechanisms, etc.

With these products, it is important to maintain a tight seal between the metal tube and the molded plastic part. For example, when the tube is used for surgical applications, it is critical that the seal between the metal tube and the plastic lens is maintained. In addition to having a tight seal, the plastic molded part must be securely attached to the tube so that the molded part does not separate from the tube. In some applications, such as surgical instruments, such a separation could cause serious harm to the patient.

In current applications, some clevis mechanisms are glued, pinned, or compressed, which may result in an insufficient seal and may not be positively secured. For example, with various cutouts formed at the end of the tube, during formation of the plastic part, overmolding extends through the cutouts. The overmolding may not completely seal the cutouts, thereby resulting in an insufficient seal.

Accordingly, there is a high demand for an end formed tube with a molded plastic part positively sealed and attached to an end thereof.

SUMMARY OF THE INVENTION

The present invention provides an end formed tube to which a molded plastic part may be attached, wherein the molded plastic part is positively attached and sealed to the end formed tube. One end of the end formed tube is rolled over 180 degrees back into the tube to form a lip which prevents the removal of the molded part. The rolled over lip portion creates a void in which plastic overmold from the plastic part is deposited, thereby creating a positive seal and attachment. Also, the end of the tube in which the lip is formed is configured in a polygonal shape, such as an octagon. This configuration provides torsional strength to the interface of the molded part and the tube, thereby creating a high "break away torque." Other aspects of the invention aspects of the invention are disclosed infra.

The present invention also provides a method of making an end formed tube with a plastic molded part attached thereto comprising the steps of: forming the lip in the tube, forming a polygon shape in the end face of the lip, filling the tube with mold to form a molded part, wherein the mold fills a void between the lip and an inside surface of the tube, and trimming the extra mold.

BRIEF DESCRIPTION OF THE DRAWINGS

These and other features and advantages of the present invention will become more apparent in view of the following detailed description in conjunction with the accompanying drawing, of which.

DETAILED DESCRIPTION OF AN ILLUSTRATIVE EMBODIMENT

The present invention will be described herein with reference to an illustrative embodiment of a end formed tube.

Figure 2:
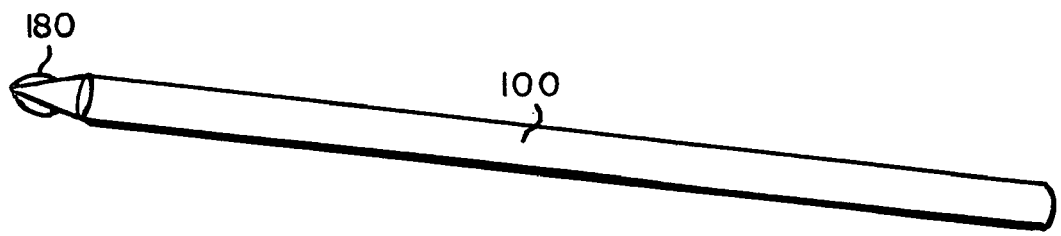
FIG. 2 is a schematic representation of the present invention showing the end formed tube and plastic molded part of a first embodiment of the invention.
Figure 1:
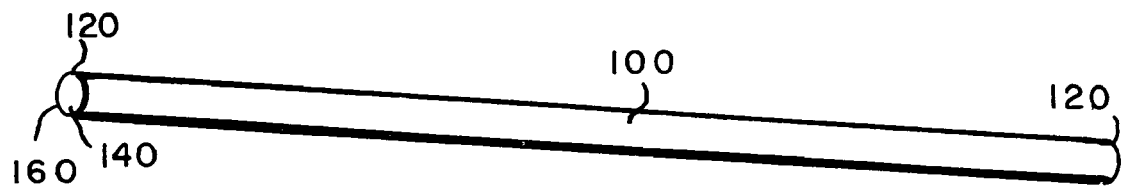
FIG. 1 is a perspective view of the present invention showing the end formed tube of the first embodiment of the invention.

FIG. 2 is a schematic representation of an end formed tube of the present invention. As shown in FIG. 1, the end formed tube 100 comprising two ends 120 and an inner portion 140. A lip portion 160 is formed at one of said ends 120. The lip portion 160 is formed by folding over the end portion 120 of the tube 100 back into the tube, as shown in FIG. 3B. As shown in FIG. 3B, preferably the lip portion 160 comprises a folded-over portion 210 formed by folding over the end portion 120 of the tube 180 degrees. However, the lip portion 160 can be folded over at various angles. Preferably, the folded over portion of the lip portion is approximately 0.020–0.060 inches. The lip portion 160 prevents the removal of the molded part. Also, the rolled over lip portion creates a void in which plastic overmold from the plastic part is deposited during molding, as discussed below, thereby creating a positive seal and further promoting positive attachment.

An end piece 180, such as a plastic lens, is secured to one of the ends 120 of the tube 100, as shown in FIG. 2. The end piece 180 can be made of any injectable type of plastic. The end piece 180 is molded to the end 120 of the tube 100. During the molding process, plastic overmolding fills the void between the lip 160 and the inner portion 140 of the tube 100. When the overmolding cools, it shrinks and pulls away from the inner portion 140 of the tube 100, thereby creating a tight seal between the inner portion 140 of the tube 100 and the end piece 180. The angle of the lip portion 160 is preferably 180 degrees to increases the amount of surface area to which the overmolding is secured, which improves the seal between the end piece 180 and the tube 100.

Figure 3A:
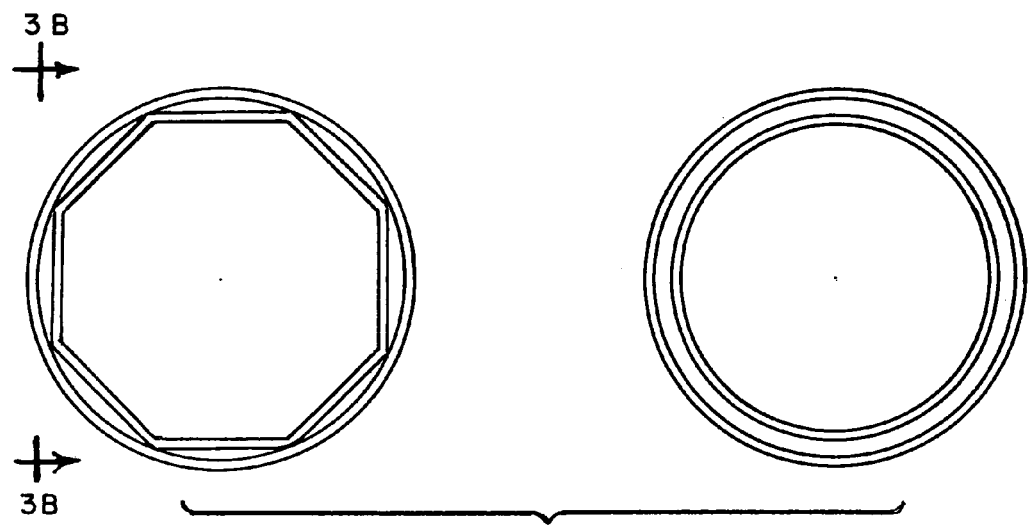
FIG. 3A is an end view of the end formed tube of the first embodiment of the invention.
Figure 3B:
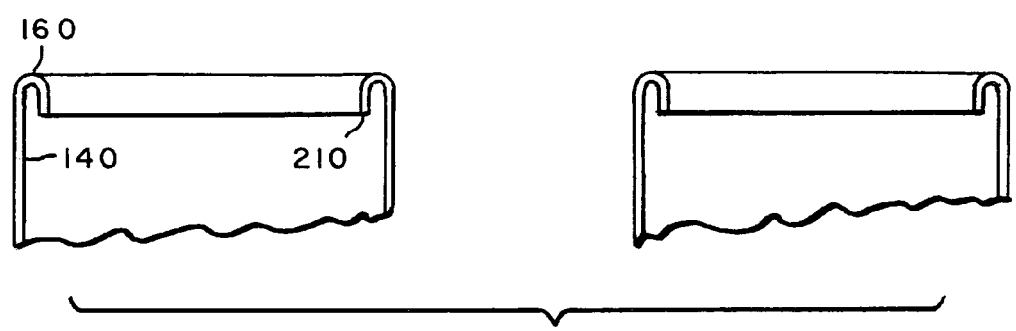
FIG. 3B is a cutaway view of FIG. 3A taken along the lines 3B—3B.

The shape of an inner surface 220 of the lip portion 160 is formed into a polygonal shape, such as an octagon, as shown in FIG. 3A. The straight sides and corners of this polygonal shape provide torsional strength to the interface of the molded part 180 and the tube 100, thereby creating a high "break away torque."

Figure 4:
FIG. 4 is an end view of the end formed tube of a second embodiment of the invention.
Figure 5:
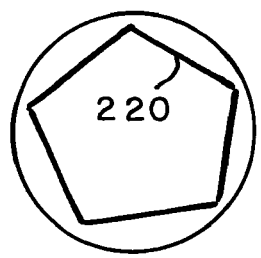
FIG. 5 is an end view of the end formed tube of a third embodiment of the invention.

The shape of the inner surface 220 of the lip portion 160 can be formed into any polygonal shape such as hexagonal or pentagonal, as shown in FIGS. 4 and 5 respectively. The straight sides and corners of these polygonal shapes also provide torsional strength to the interface of the molded part 180 and the tube 100, thereby creating a high "break away torque."

The present invention also provides a method of making an end formed tube with a plastic molded part attached thereto comprising the steps of: forming the lip in the tube, forming a polygon shape in the end face of the lip, filling the tube with mold to form a molded part, wherein the mold fills a void between the lip and an inside surface of the tube, and trimming the extra mold. The step of forming the lip can be done as a multiple step process wherein the lip is gradually formed to the desired angle. The steps of forming the lip and the polygon shape can be done with a mandrel, or by a similar machining process.

Although the invention has been shown and described with respect to exemplary embodiments thereof, various other changes, additions and omissions in the form and detail thereof may be made therein without departing from the spirit and scope of the invention.

What is claimed is:

1. An end formed tube comprising:

a hollow tube having an inner portion and two ends; and a lip portion formed on one of said two ends, wherein said lip portion comprises a folded-over portion formed by folding over an end portion of said tube back into said tube towards an inside of said tube, wherein an inner surface of said folded-over portion has a polygonal shape.

2. An end formed tube comprising:

a hollow tube having an inner portion and two ends;

a lip portion formed on one of said two ends, wherein said lip portion comprises a fold-over portion formed by folding over an end portion of said tube back into the tube towards an inside of said tube, wherein an inner surface of said folded over portion has a polygonal shape; and an end piece secured to said lip portion.

3. An end formed tube as set forth in claim 1, wherein said polygonal shape is octagonal.

4. An end formed tube as set forth in claim 2, wherein said polygonal shape is octagonal.

5. An end formed tube as set forth in claim 1, wherein said polygonal shape is chosen from the group comprising hexagonal and pentagonal.

6. An end formed tube as set forth in claim 2, wherein said polygonal shape is chosen from the group comprising hexagonal and pentagonal.

7. An end formed tube as set forth in claim 1, wherein said lip portion is folded over 180 degrees.

8. An end formed tube as set forth in claim 2, wherein said lip portion is folded over 180 degrees.

* * * * *